United States Patent
White

(10) Patent No.: US 11,987,544 B2
(45) Date of Patent: May 21, 2024

(54) DEVICE AND METHOD FOR EXTRACTION OF PURE COMPOUNDS

(71) Applicant: Applied Extracts Inc., San Mateo, CA (US)

(72) Inventor: James Robert White, San Mateo, CA (US)

(73) Assignee: APPLIED EXTRACTS INC., San Mateo, CA (US)

(*) Notice: Subject to any disclaimer, the term of this patent is extended or adjusted under 35 U.S.C. 154(b) by 0 days.

(21) Appl. No.: 17/987,857

(22) Filed: Nov. 15, 2022

(65) Prior Publication Data

US 2023/0080791 A1  Mar. 16, 2023

Related U.S. Application Data

(62) Division of application No. 17/102,140, filed on Nov. 23, 2020, now Pat. No. 11,814,345.

(Continued)

(51) Int. Cl.
*C07C 37/68* (2006.01)
*B01D 11/02* (2006.01)
(Continued)

(52) U.S. Cl.
CPC ........ *C07C 37/685* (2013.01); *B01D 11/0203* (2013.01); *B01D 11/0207* (2013.01);
(Continued)

(58) Field of Classification Search
CPC .............. C07C 37/685; B01D 11/0203; B01D 11/0207; B01D 11/028; B01D 11/0292; B01D 29/11; C07D 311/80
(Continued)

(56) References Cited

U.S. PATENT DOCUMENTS 5,525,746 A * 6/1996 Franke ............... B01D 11/0219
554/20
2013/0098080 A1 4/2013 Biancardi
(Continued)

FOREIGN PATENT DOCUMENTS

CN 114423503 A * 4/2022 ........... A23L 33/105
EA 020623 B1 12/2014
(Continued)

OTHER PUBLICATIONS

Office Action 1 for U.S. Appl. No. 17/102,140, dated Sep. 22, 2022.
(Continued)

*Primary Examiner* — Terrell H Matthews
(74) *Attorney, Agent, or Firm* — TOPE-MCKAY & ASSOCIATES

(57) ABSTRACT

Described is an extraction device for extracting compounds from plant material and a method for using such an extraction device. The extraction device comprises an extraction tank receiving plant material and dissolving soluble compounds inside the plant material into a solvent to form a micelle. A series of fluidly connected separation chambers separate purified compounds from the micelle, resulting in purified compounds in each of the separation chambers and solvent. A heat exchanger and a chilled reservoir are used for cooling and storing the solvent. A pump is used for pumping and circulating the solvent into the extraction device. Finally, a control system automatically controls temperature and flow in the extraction device.

1 Claim, 6 Drawing Sheets

Related U.S. Application Data

(60) Provisional application No. 62/938,801, filed on Nov. 21, 2019.

(51) Int. Cl.
*B01D 29/11* (2006.01)
*C07D 311/80* (2006.01)

(52) U.S. Cl.
CPC ........ *B01D 11/028* (2013.01); *B01D 11/0292* (2013.01); *B01D 29/11* (2013.01); *C07D 311/80* (2013.01)

(58) Field of Classification Search
USPC .......................................................... 549/390
See application file for complete search history.

(56) References Cited

U.S. PATENT DOCUMENTS

| | | | | |
|---|---|---|---|---|
| 2018/0099235 | A1* | 4/2018 | Joseph | B01D 11/028 |
| 2019/0153484 | A1* | 5/2019 | Bray | C12P 17/06 |
| 2021/0069610 | A1 | 3/2021 | Pierce | |
| 2021/0187413 | A1 | 6/2021 | Marienau | |

FOREIGN PATENT DOCUMENTS

| | | | | |
|---|---|---|---|---|
| EP | 2391698 | B1 * | 9/2018 | ........... B01D 17/042 |
| KR | 20140100711 | A | 8/2014 | |
| KR | 20150094759 | A | 8/2015 | |
| KR | 101700175 | B1 | 1/2017 | |
| TW | 202041261 | A | 11/2020 | |
| WO | WO-2017193072 | A1 * | 11/2017 | ............. A23L 29/03 |
| WO | WO2018190935 | A1 | 10/2018 | |
| WO | WO2018215520 | A1 | 11/2018 | |

OTHER PUBLICATIONS

Response to Office Action 1 for U.S. Appl. No. 17/102,140, dated Nov. 15, 2022.
Office Action 2 for U.S. Appl. No. 17/102,140, dated Mar. 22, 2023.
Response to Office Action 2 for U.S. Appl. No. 17/102,140, dated Jun. 22, 2023.
Notice of Allowance for U.S. Appl. No. 17/102,140, dated Jul. 14, 2023.

* cited by examiner

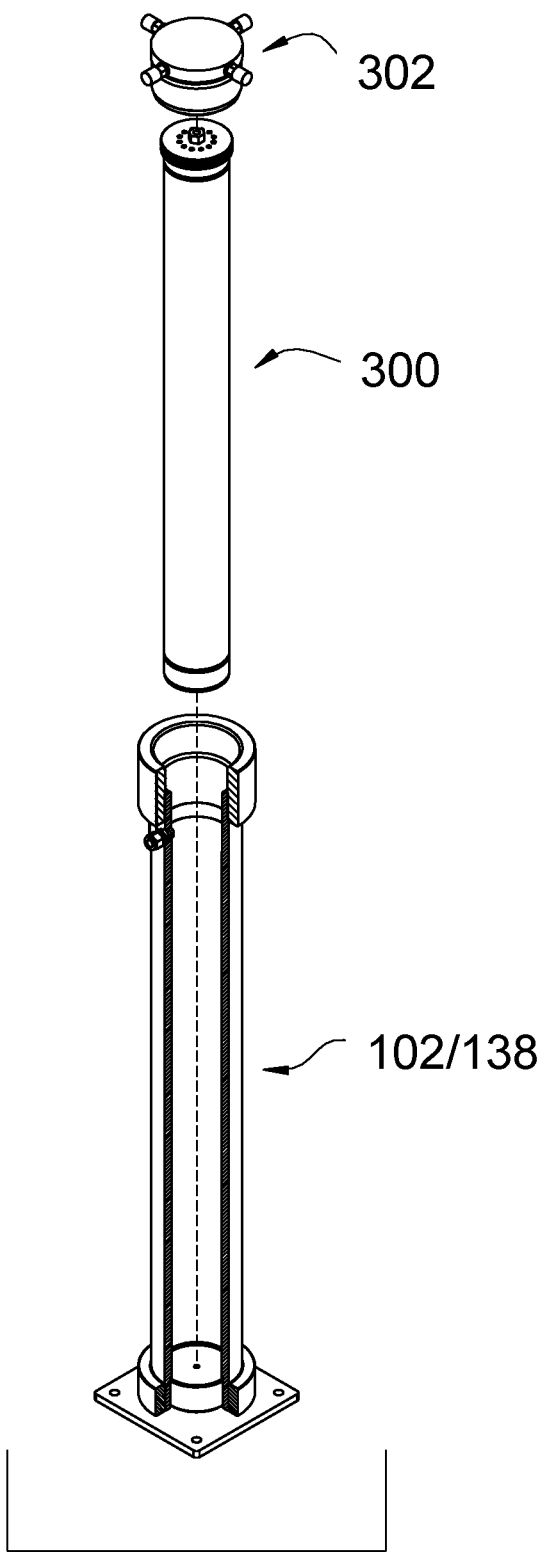
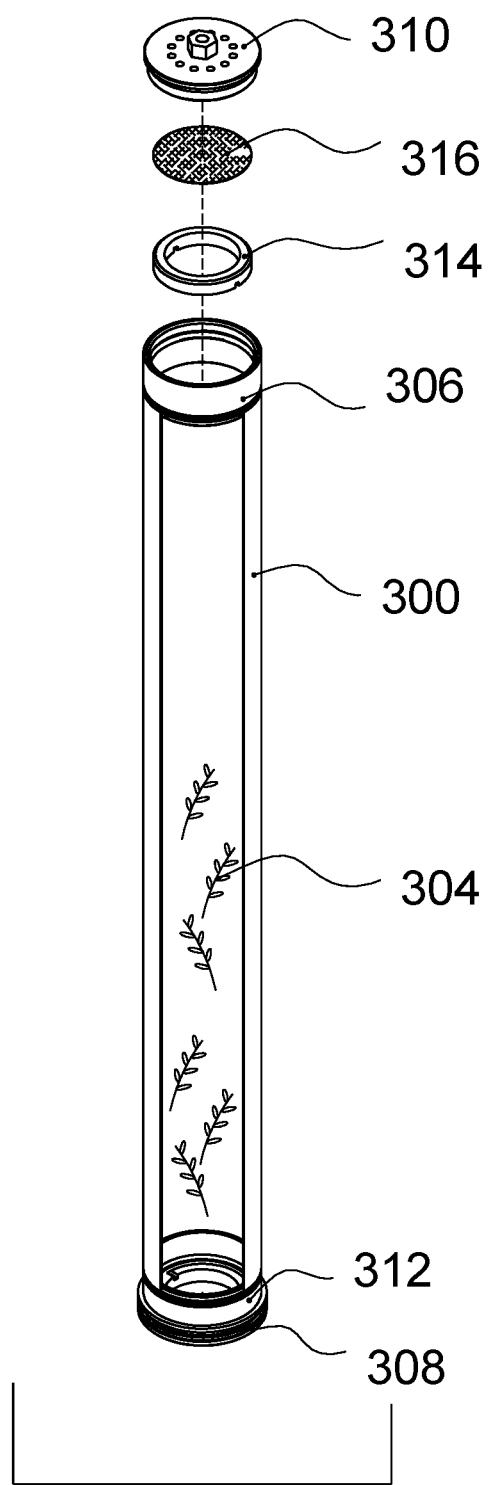
Fig. 3
Fig. 4

DEVICE AND METHOD FOR EXTRACTION OF PURE COMPOUNDS

PRIORITY CLAIM

The present application is Divisional application of U.S. application Ser. No. 17/102,140, filed on Nov. 23, 2020, which is a Non-Provisional Utility patent application of U.S. Provisional Application No. 62/938,801, filed on Nov. 21, 2019, the entirety of which are incorporated herein by reference.

BACKGROUND OF THE INVENTION

(1) Field of Invention

This invention relates to the extraction of soluble compounds from plant material and, more specifically, to a device and method for extracting purified compounds from a plant using carbon dioxide as a solvent to produce the pure compounds in an efficient and cost-effective manner.

(2) Description of Related Art

The extraction of purified compounds from plant material is of general interest to many industries. Common applications of this invention are the extraction and purification of flavorings, perfumes, nutraceuticals and pharmaceutical ingredients, essential oils, botanical oils and similar compounds. One example of a class of compounds that are of commercial interest is terpenes, which are naturally occurring compounds that can define the characteristic aroma of a plant. Another class of compounds that are of commercial interest are cannabinoids. These compounds may include psychoactive compounds such as tetrahydrocannabinol (THC) and non-psychoactive compounds such as cannabidiol (CBD). Many plants also contain significant amounts of wax, resin, chlorophyll, and cellulose.

It is generally desirable to separate commercially valuable compounds such as terpenes or cannabinoids from commercially undesirable compounds such as waxes, resins, chlorophyll and cellulose. Many extraction processes are known in the art. However, most suffer from a general lack of selectivity. As a result, it is often the case that desirable and undesirable compounds are extracted simultaneously. The operator must then perform additional extraction and separation steps to obtain the final desired pure compounds. This is time consuming, expensive and reduces overall yield and throughput, and increases the capital cost of equipment required.

Thus, devices and methods that can quickly and cost-effectively produce pure compounds with minimal operator intervention and maximum yield are desirable and advantageous. Numerous super-critical and sub-critical carbon dioxide extraction machines are known in the art. In typical machines currently available on the market, selective extraction of cannabinoids and waxes is not possible. The machines are configured to produce a 'total extract' as they have only one separation chamber that collects all extracted compounds. Some degree of selectivity can be obtained by operating the machine at varying pressure and temperatures in the extraction tank, collecting each extracted fraction individually, performing a second extraction at a different pressure and temperature, collecting that second extract, and so forth until the desired extraction process has been completed. However, this approach is very labor intensive and time consuming. Attempting selective extraction of desired compounds in this manner can require many hours to achieve complete extraction. Thus, machines that operate in this fashion are slow, ineffective and uneconomical.

Yet other techniques to purify extracted compounds require the use of additional expensive and specialized equipment to achieve the desired result. For example, a so-called 'total extract' may be produced in any suitable extraction device. A second step, preparative chromatography, is known in the art, and may be used to selectively separate cannabinoids or other compounds into substantially pure fractions. However, this method is extremely expensive and time consuming, and is not commercially viable for large-scale production as the cost of the column packing material is high and this material is rapidly fouled by other compounds in the 'total extract.' In contrast, using the preferred embodiment disclosed herein, a pure solid crystalline cannabinoid extract was produced from plant material in a single extraction step.

Another common method for post-extraction processing is distillation. This may take the form of wiped-film distillation, molecular distillation, vacuum distillation or any other suitable means.

Thus, a continuing need exists for a device and method for extracting purified compounds from a plant in an efficient and cost-effective manner.

SUMMARY OF INVENTION

This invention relates to the extraction of soluble compounds from material. More specifically, it relates to the extraction of purified or substantially purified compounds from plant material using an extraction device. An example of this is the extraction of purified cannabinoids and terpenes from the *Cannabis* plant. Furthermore, it relates to the use of carbon dioxide as a solvent to produce pure compounds in an efficient and cost-effective manner and at large scale.

In one aspect, the extraction device comprises an extraction tank. The extraction tank is operable for receiving plant material and dissolving soluble compounds inside the plant material into a solvent to form a micelle. A series of fluidly connected separation chambers is included to separate purified compounds from the micelle, resulting in purified compounds in each of the separation chambers and solvent. A heat exchanger and a chilled reservoir are also included for cooling and storing the solvent. A pump is used for pumping and circulating the solvent into the extraction device. Finally, a control system is included to automatically control temperature and flow in the extraction device.

In another aspect, the solvent is a liquid and supercritical carbon dioxide.

In another aspect, the extraction tank includes a means to control the pressure and temperature inside the extraction tank.

In yet another aspect, each separation chamber includes a means to control the pressure and temperature inside the extraction tank.

In another aspect, each separation chamber includes an internal filter in fluid communication with an outlet.

The present invention also provides method for extracting substantially purified compounds from solid material, comprising acts of passing a solvent in a supercritical state over the solid material to form a micelle; collecting a first fraction of a compound in a first separation chamber by lowering a temperature of the micelle to a critical point of the solvent; collecting a second fraction by further lowering the temperature and pressure of the micelle in a second collection chamber to below the critical point of the solvent; and collecting a third fraction by further lowering the temperature of the micelle in a third separation chamber. In an aspect, the solid material is a decarboxylated plant material.

In another aspect, the decarboxylated plant material is formed by performing acts of freezing a plant material with liquid nitrogen to form frozen plant material; grinding the frozen plant material to form ground plant material; and decarboxylating the ground plant material in a vacuum oven to form the decarboxylated plant material.

Finally, as can be appreciated by one skilled in the art, the present invention also comprises a method for forming and using the invention described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 3 is an illustration of sleeves and an extraction tank according to various embodiments of the present invention, depicting a process by which plant material is placed in the removable sleeves and inserted into an extraction tank;

FIG. 4 is an illustration of sleeves and an extraction tank according to various embodiments of the present invention, depicting a process by which plant material is placed in the removable sleeves and inserted into an extraction tank;

DETAILED DESCRIPTION

Figure 1:
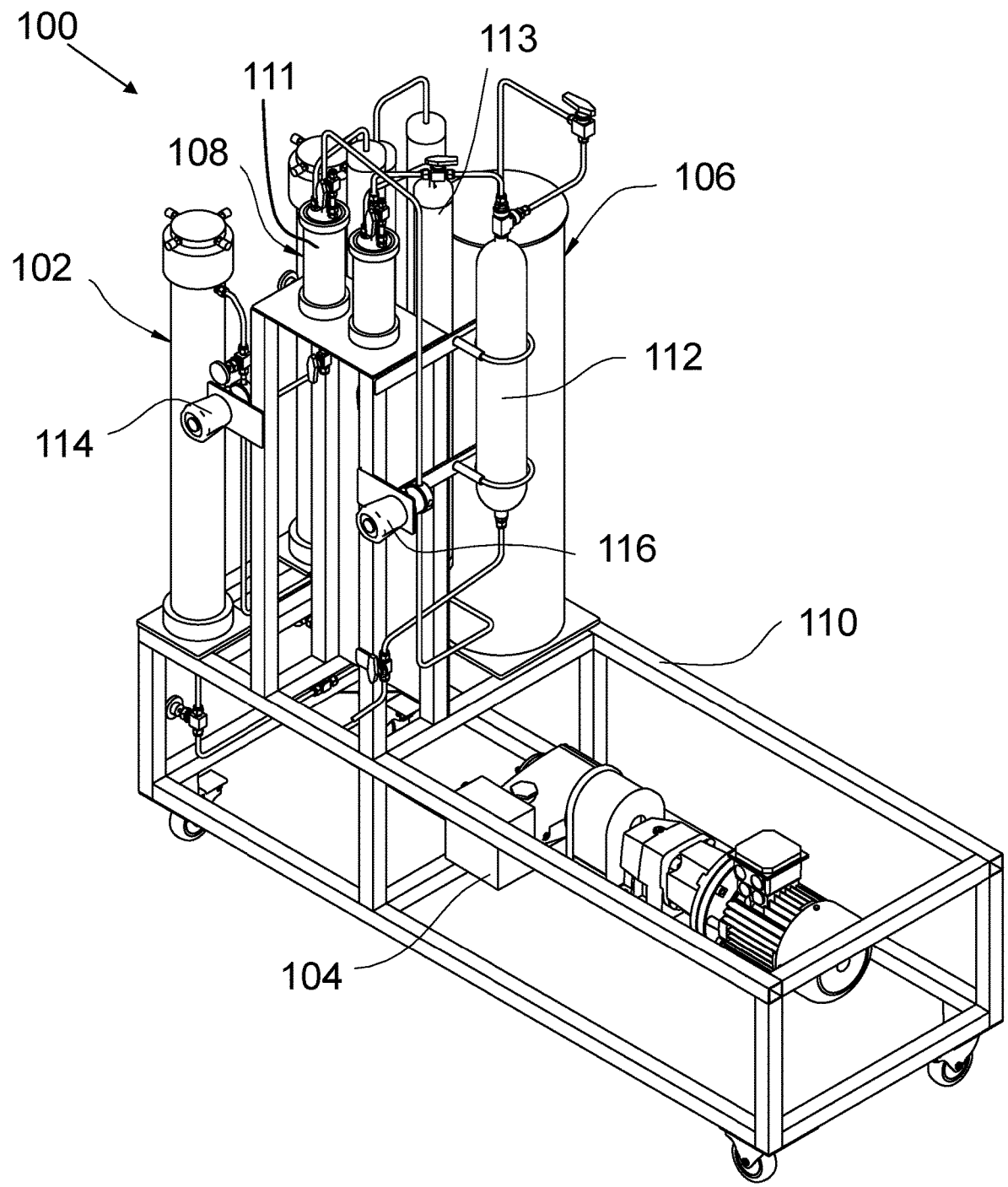
FIG. 1 is an illustration of an extraction device for extraction of pure compounds according to an embodiment of the present invention.

This invention relates to the extraction of soluble compounds from material. More specifically, it relates to the extraction of purified or substantially purified compounds from plant material. An example of this is the extraction of purified cannabinoids and terpenes from the *Cannabis* plant. Furthermore, it relates to the use of carbon dioxide as a solvent to produce pure compounds in an efficient and cost-effective manner and at large scale. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Description

This disclosure is directed to an extraction device and method for extraction of soluble compounds from plant material using carbon dioxide as a solvent to produce pure compounds in an efficient and cost-effective manner and at large scale. A non-limiting example of this is the extraction of purified cannabinoids and terpenes from the *Cannabis* plant.

The disclosed extraction device is an optimized closed-loop supercritical carbon dioxide extraction machine that, in combination with the extraction method disclosed herein, can produce distinct and purified fractions of cannabinoids, pure or substantially pure fractions of waxes and resins, and pure fractions of terpenes. However, this technique may be applicable to other classes of compounds and the preceding general description should not be construed as limiting the scope or applicability of my invention in any way.

As shown in FIG. 1, the extraction device 100 is a closed-loop super critical carbon dioxide extraction machine that employs a high-pressure vessel, called an extraction tank 102, into which plant material is deposited. The extraction device 100 includes all of the relevant components to extract pure compounds placed within the extraction tank 102. For example and in some embodiments, the extraction device 100 also includes high pressure pump 104, a condenser assembly 106, a separator assembly 108 (having a series of separation chambers, a frame assembly 110, a third separator chamber 112, an inline heater 113, a high-pressure backpressure regulator 114, and a low-pressure backpressure regulator 116.

In operation, carbon dioxide is delivered to the extraction tank 102 using a high-pressure pump 104. Each extraction tank 102 has means to control the pressure and temperature inside the extraction tank. As a non-limiting example, in-line with the pump 104 may be a heater, which can heat the carbon dioxide to the desired extraction temperature. Further, at the outlet of the extraction tank 102 is desirably a flow restriction, which restricts the flow of carbon dioxide and causes the pressure in the extraction tank 102 to increase when the pump 104 is operating. Thus, the pressure and temperature of each extraction tank 102 can be controlled as desired. This flow restriction may take the form of a valve, an orifice, the high-pressure backpressure regulator 114, or any other suitable device. The extraction tank 102 may further be heated via any suitable technique or device, such as electric heater jacket, water jacket, steam or other means. Plant material is deposited into the extraction tank 102 either directly, or in a porous mesh bag, or in a metal sleeve or cylinder that permits rapid removal of spent material. A solvent is also placed within the extraction tank 102. Desirably, the solvent is any suitable solvent, a non-limiting example of which includes the carbon dioxide as described below. Soluble compounds inside the plant material dissolve into the solvent, and are conveyed by the pumped solvent into a series of separation chambers.

Turning now to the properties of the solvent used for extraction. If the pressure and temperature of the carbon dioxide exceed the critical point of that fluid, it is said to be "super critical." If the pressure or temperature of the carbon dioxide do not exceed the critical point, the carbon dioxide may instead exist in a liquid, gas or solid phase inside the extraction tank, or in a combination of those phases. However, it is generally known in the art that carbon dioxide is a weak solvent in it's liquid phase and a good solvent in it's super critical phase. Thus, in the interest of extraction efficiency, the device 100 uses either super critical carbon dioxide as a solvent to quickly extract desired compounds, or liquid phase carbon dioxide to extract low boiling point compounds such as terpenes.

It is also generally known that super critical carbon dioxide is an effective and versatile solvent that can readily dissolve cannabinoids, waxes, resins, chlorophyll and terpenes, but does not effectively dissolve cellulosic plant matter. Carbon dioxide may also be combined with other solvents such as hydrocarbons (butane, propane, or hexane for example), ethanol, vegetable oil, or water. By doing so, an operator may adjust the solvent properties of carbon dioxide to obtain other desirable extraction properties. However, the addition of these so-called co-solvents further requires separation of the co-solvent from the desired extracted compound. Although the disclosed method does not make use of a co-solvent, this is not intended to limit the potential use of co-solvents in practicing the invention of the present disclosure.

Returning to the design of the extraction device and as shown between FIGS. 1 and 2, the carbon dioxide solvent passes through an inlet valve 103 and through the first extraction tank 102 containing plant matter (e.g., decarboxylated plant material, see below), at which point soluble compounds are dissolved into the solvent, forming a micelle. The flowing solvent exits the extraction tank 102 and its outlet valve 105 containing plant matter and passes through the flow restriction device (e.g., high-pressure backpressure regulator 114). The micelle now proceeds into a first separation chamber 111 in the separator assembly 108. In this first separation chamber 111, the pressure and temperature of the micelle are controlled such that the carbon dioxide solvent is at the critical temperature of carbon dioxide, 304.25K. With the micelle in this state, it is noted that the cannabinoid compounds are preferentially deposited in the separation chamber 111 in a pure, dry, and substantially wax-free form, while waxes and terpenes remain in solution. Thus, the first separation of cannabinoids, is accomplished and can be collected via a separator outlet valve 113. For example, an operator could open the valve 131 and the oil or extract will shoot out under pressure into a desired collection container.

A key aspect of the present invention is the use of effective filtration between successive separation stages. Although not limited thereto, an example of an effective filter used in practicing this invention is a porous polytetrafluoroethylene (PTFE) filter element of any desired size. For example, a pore diameter in the filter element of between 5 microns and 50 microns may be used. Alternatively, any other suitable filter pore diameter may be used. However, the filter element should generally be capable of preventing the passage of precipitated compounds between separation stages. Many super critical $CO_2$ extraction machines have multiple separation chambers which may be controlled to varying pressure and temperature setpoints. However, these machines are ineffective at separating pure compounds because they lack the inter-separator filtration as used in the present disclosure. The filter is depicted, for example, as element 510 in FIG. 5, which filters precipitated compounds from passing between separation chambers. Thus, the present invention is desirably formed to include multiple extraction and separator chambers as illustrated further in FIG. 2. In this aspect, the device 100 desirably includes a second extraction tank 138 with the relevant inlet and outlet valves 140 and 142, respectively, to operate in a similar manner as described above with respect to the first extraction tank 102.

Figure 2:
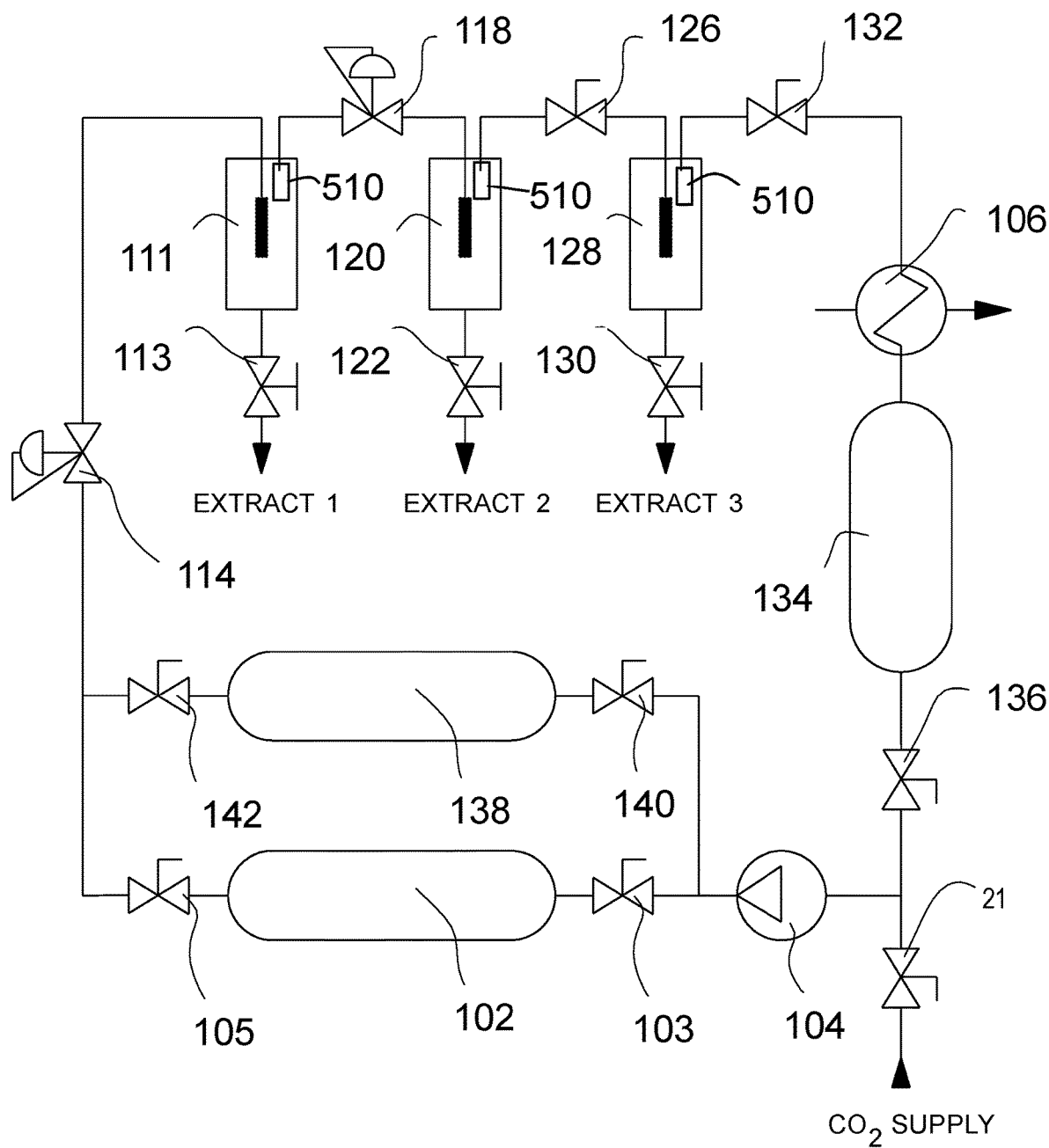
FIG. 2 is a piping and instrumentation diagram (P&ID) of the extraction device for extraction of pure compounds according to an embodiment of the present invention.

As shown in FIG. 2, the micelle now passes through a second flow restriction 118 (e.g., backpressure regulator) and into a second separation chamber 120. In one aspect, this second separation chamber 120 is controlled to a low temperature and pressure, for example, 11° C. and 750 psi. At this point, waxes and resins are generally insoluble in the liquid carbon dioxide solvent, and will precipitate into the second separation chamber 120 and can be collected as desired via an outlet valve 122. A second filter element 510, similar in design to the first, is present at the outlet of the separation chamber, and substantially prevents precipitated extracts from passing into the third separation chamber 128 via a user operable shutoff valve 126.

The third separation chamber 128 is designed to recover terpene compounds. Terpenes are often readily soluble in liquid and supercritical carbon dioxide due to their low boiling point and miscibility with liquid carbon dioxide. However, it has been observed that the solubility of terpenes decreases substantially as the temperature of the liquid carbon dioxide is lowered. When the liquid carbon dioxide is further cooled, terpenes precipitate into the third separation chamber 128 and are readily recovered by means of a valve 130 or tap at the bottom of the third separation chamber 128. The collection temperature of the terpenes may be at any temperature, but is generally most effective when the liquid carbon dioxide is cooled to 10° C. or less, and very effective at −5° C. or less. The third separation chamber 128 may be sized such that the cold, liquid $CO_2$ will reside in the tank for a period of minutes to allow for more complete separation of the terpenes and carbon dioxide. It should noted that each of the separation chambers has means to control the pressure and temperature inside each separation chamber. As a non-limiting example, each separation chamber has its own heater (e.g., in line heater, heater jacket, etc.) that is separately controllable, as well as its own pressure regulator. It should be noted that the extraction device can be outfitted with a control system to automatically control temperature and flow in the extraction device through the various tanks and chambers as desired. As understood by those skilled in the art, such a control system is, for example, a computer controller with sensors that can monitor and adjust pressure at the various heaters, regulators, valves, etc., as desired to maintain the temperature and pressure at desired ranges.

When the shutoff valve is opened 132, the carbon dioxide solvent, substantially devoid of any entrained solute, passes through a cooling coil in a condenser assembly 106 surrounded by chilled coolant delivered from a chiller or other suitable cooling apparatus, and into a chilled reservoir 134 for storage. This chilled reservoir 134 provides a continuous flow of cold, liquid carbon dioxide into the pump 104 (when the relevant shutoff valve 136 is opened), and the extraction cycle continues. The duration of a typical extraction cycle in my invention is one hour, although this time may vary substantially with the composition of the plant matter used, the pumping speed, the extraction tank size, and other considerations.

Thus, comparing the efficiency of the present invention to other typical extraction machines known in the art, the present invention is faster, requires less operator intervention, requires little to no additional capital equipment to produce marketable extracted compounds, and can produce refined compounds in a highly selective manner.

For further understanding, FIGS. 3 and 4 provide illustrations of sleeves 300 and an extraction tank 102 or 138, depicting a process by which plant material is placed in the removable sleeves and inserted into an extraction tank 102 or 138, where it is sealed therein via a lid 302 or other similar device or technique. The sleeve 300 is any suitable mechanism or device that is operable for containing the plant material 304 therein for extraction. For example and as shown in FIG. 4, the sleeve 300 includes an outer ring 306, a bottom lid 308, a top lid 310, a bottom ring 312, a locking ring 314 and a mesh screen 316. The outer ring 306 is used for providing mating threads for the head 310 to screw into, while the bottom ring 312 performs the same function as outer ring 306 but on the bottom side of the sleeve, and locking ring 314 is used to hold the mesh screen 316 in place. The mesh screen 316 operates to prevent particles of plant matter from flowing out of the sleeve and into the separators.

Figure 5:
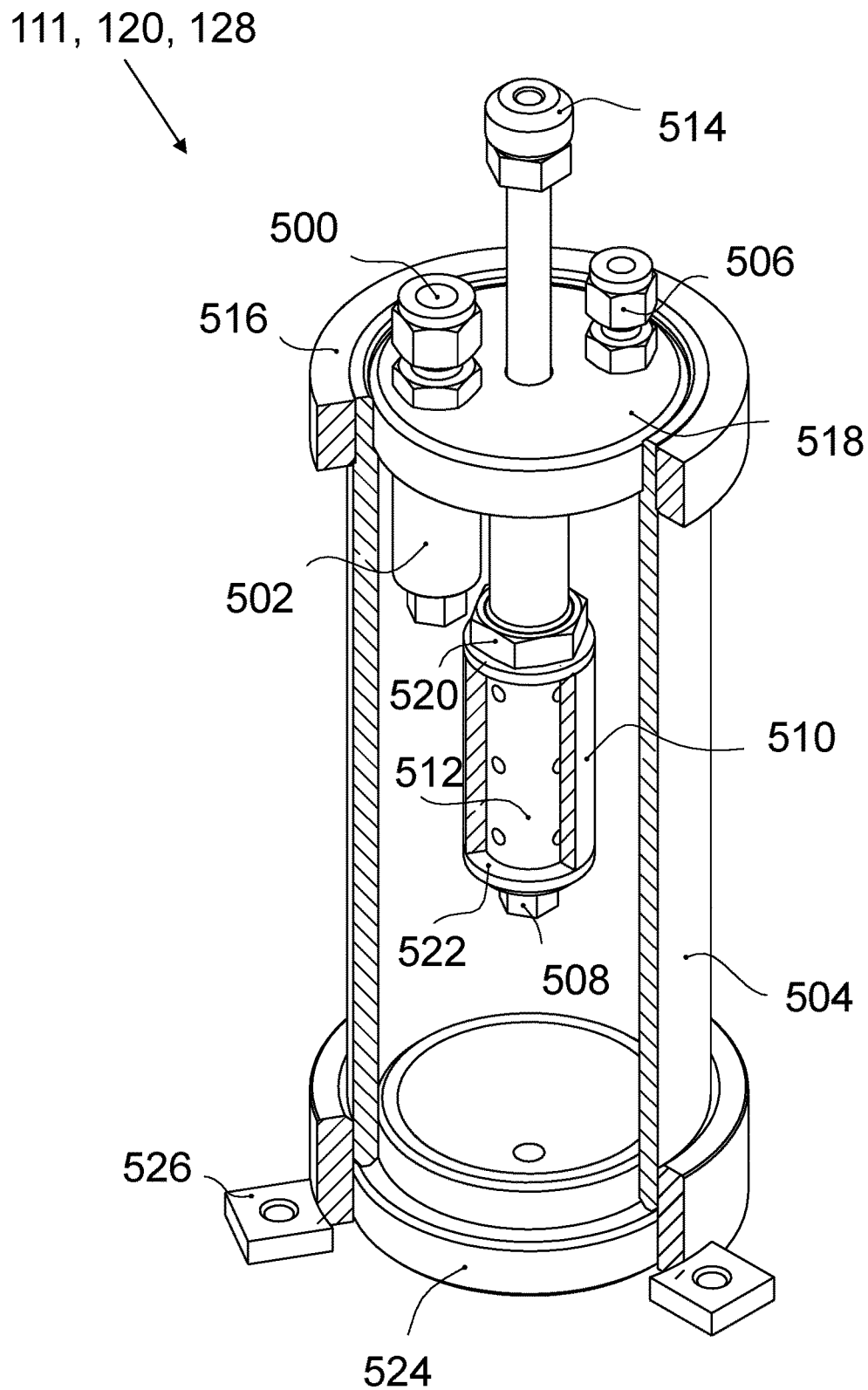
FIG. 5 is an interior-view illustration of a separation chamber according to various embodiments of the present invention.

FIG. 5 provides an interior-view illustration of a separation chamber 111, 120, 128. The separation chamber 111, 120, and 128 is formed to separate the components as described above. In one aspect, the separation chamber 111, 120 and 128 includes an inlet port 500 that introduces the material to an injector port 502. In one aspect, the inlet port 500 is oriented such that the flow entering the separator enters with a velocity that is substantially tangential to the wall of the separator at the entry point. The injector port 502 introduces the material into the interior of the separation body 504 for separation. In another aspect, to relieve pressure when necessary, a vent portion 506 is included that vents from the separation body 504 to the exterior. A stem nut 508 secures the filter body 510 against the outlet stem 512. A filter locking washer 520 and bottom washer 522 are also depicted. The filter body 512 substantially prevents precipitated extracts from passing through filter body and into the outlet stem 512 (via orifices formed in the outlet stem 512), where the material can be passed from an outlet port 514 into successive separation chambers or to the chilled reservoir 134. Also depicted are a compression ring 516 that secures the top cover 518 within the body 504. Finally, a separator bottom lid 524 can be affixed with the body 504 using any suitable mechanism or device, such as a foot 526 that can be bolted to the frame or any other component.

Figure 6:
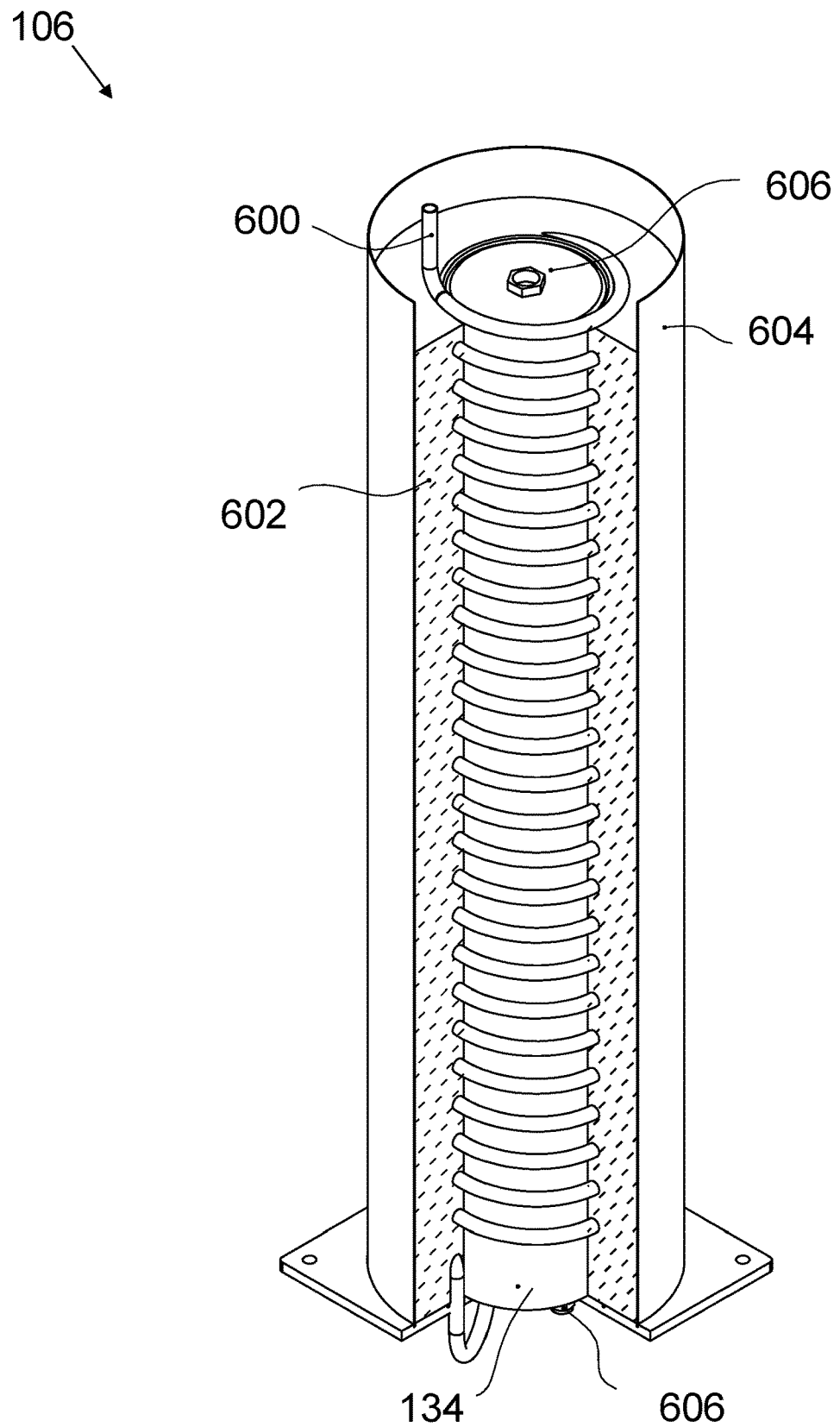
FIG. 6 is an interior-view illustration depicting a solvent storage reservoir with integrated cooling coil and a coolant jacket according to various embodiments of the present invention.

As noted above and as shown in FIG. 6, the carbon dioxide solvent, substantially devoid of any entrained solute, passes through a cooling coil (i.e., heat exchanger tube 600) in the condenser assembly 106. The heat exchanger tube 600 is surrounded by a coolant fluid 602 that is contained within an outer jacket 604 of the condenser assembly 106. In one aspect, the heat exchanger tube 600 wraps around the reservoir 134, where the chilled carbon dioxide solvent is deposited after passing through the heat exchanger tube 600. Thus, in this aspect, the heat exchanger tube 600 is in fluid communication with the reservoir 134. The chilled carbon dioxide solvent can then be selectively passed from the reservoir outlet port 606 and back to the pump 104 for continuous use in extraction. Also depicted is the reservoir lid 608.

Figure 7:
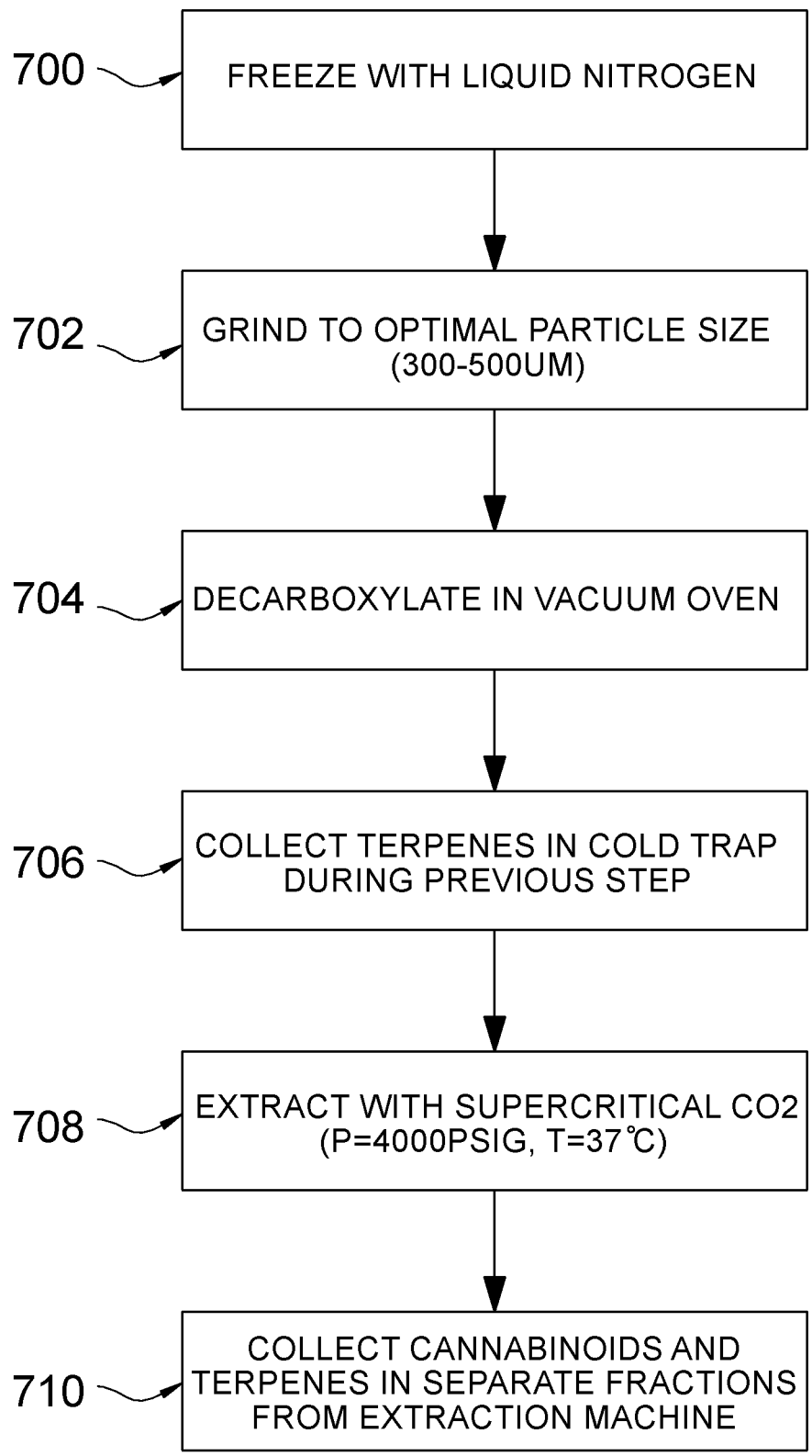
FIG. 7 is a flow chart depicting a process for rapid extraction of pure cannabinoids and terpenes according to various embodiments of the present invention.

As described above and as further depicted in FIG. 7, the present invention provides an efficient process for rapid extraction of pure cannabinoids and terpenes. In one aspect, the process begins with the plant material being frozen 700 with liquid nitrogen. Thereafter, the frozen plant material is ground 702 to an optimal particle size for extraction, desirably between 300 and 500 micrometers. Optionally, the ground plant material is then decarboxylated 704 in a vacuum oven to alter the plant material before extraction. Terpenes can also be collected 706 using a cold trap during the decarboxylation 704 process, leaving remaining decarboxylated plant material. The remaining decarboxylated plant material is then introduced into the extraction tank of the present invention (as described above and illustrated), where pure compounds are extracted 708. At the end of the process, cannabinoids and terpenes are then collected 710 in separate fractions from the extraction device.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A method for extracting substantially purified compounds from solid material, comprising acts of;
    passing a solvent in a supercritical state over the solid material to form a micelle;
    collecting a first fraction of a compound in a first separation chamber by lowering a temperature of the micelle to a critical point of the solvent;
    collecting a second fraction by further lowering the temperature and pressure of the micelle in a second separation chamber to below the critical point of the solvent;
    collecting a third fraction by further lowering the temperature of the micelle in a third separation chamber;
    wherein the solid material is a decarboxylated plant material; and wherein the decarboxylated plant material is formed by performing acts of:
  freezing a plant material with liquid nitrogen to form frozen plant material;
  grinding the frozen plant material to form ground plant material; and
  decarboxylating the ground plant material in a vacuum oven to form the decarboxylated plant material.

\* \* \* \* \*